(12) United States Patent
Gunderson

(10) Patent No.: US 9,199,078 B1
(45) Date of Patent: Dec. 1, 2015

(54) IDENTIFYING LEAD PROBLEMS USING AMPLITUDES OF FAR-FIELD CARDIAC EVENTS

(71) Applicant: Medtronic, Inc., Minneapolis, MN (US)

(72) Inventor: Bruce D. Gunderson, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/522,722

(22) Filed: Oct. 24, 2014

(51) Int. Cl.
- A61N 1/00 (2006.01)
- A61N 1/08 (2006.01)
- A61N 1/39 (2006.01)
- A61N 1/05 (2006.01)

(52) U.S. Cl.
CPC .............. *A61N 1/08* (2013.01); *A61N 1/0563* (2013.01); *A61N 1/3925* (2013.01); *A61N 2001/083* (2013.01)

(58) Field of Classification Search
CPC ... A61N 2001/083; A61N 1/37; A61N 1/362; A61N 1/08; A61N 1/3925; A61N 1/0563
See application file for complete search history.

(56) References Cited

U.S. PATENT DOCUMENTS

| | | | |
|---|---|---|---|
| 3,602,215 | A | 8/1971 | Parnell |
| 5,344,430 | A | 9/1994 | Berg |
| 5,354,316 | A | 10/1994 | Keimel |
| 5,545,186 | A | 8/1996 | Olson |
| 5,549,646 | A | 8/1996 | Katz |
| 5,593,431 | A | 1/1997 | Sheldon |
| 5,755,742 | A | 5/1998 | Schuelke |
| 5,776,168 | A | 7/1998 | Gunderson |
| 5,814,088 | A | 9/1998 | Paul |
| 5,897,577 | A | 4/1999 | Cinbis et al. |
| 5,957,861 | A | 9/1999 | Combs et al. |
| 5,959,861 | A | 9/1999 | Kaneko |
| 6,393,316 | B1 | 5/2002 | Gillberg |
| 6,745,068 | B2 | 6/2004 | Koyrakh et al. |
| 7,047,083 | B2 | 5/2006 | Gunderson |
| 7,120,493 | B2 | 10/2006 | Propp |
| 7,242,978 | B2 | 7/2007 | Cao |
| 7,266,409 | B2 | 9/2007 | Gunderson |
| 7,277,757 | B2 | 10/2007 | Casavant |

(Continued)

FOREIGN PATENT DOCUMENTS

WO 2006119136 A1 11/2006

OTHER PUBLICATIONS

Leong et al., "Unrecognized Failure of a Narrow Caliber Defibrillation Lead: The Role of Defibrillation Threshold Testing in Identifying an Unprotected Individual", PACE, vol. 00, 2012, 2 pages.

*Primary Examiner* — Scott Getzow
(74) *Attorney, Agent, or Firm* — Michael J. Ostrom

(57) ABSTRACT

An implantable medical device capable of sensing cardiac signals and delivering cardiac electrical stimulation therapies is enabled to detect a short circuit condition on a sensing or therapy vector. A cardiac signal is sensed by a sensing module coupled to electrodes. A control module detects a short circuit condition in response to a significant drop in amplitude of far-field cardiac events coincident to near-field cardiac events. In some instances, the short circuit condition is detected in response an abnormal impedance on the far-field sensing vector and/or a matching morphology of the far-field cardiac electrical signal including the coincident FF cardiac event in addition to the significant drop in amplitude of the coincident FF cardiac events.

21 Claims, 9 Drawing Sheets

(56) References Cited

U.S. PATENT DOCUMENTS

| | | |
|---|---|---|
| 7,289,851 B2 | 10/2007 | Gunderson |
| 7,454,249 B1 | 11/2008 | Bornzin |
| 7,515,961 B2 | 4/2009 | Germanson |
| 7,706,869 B2 | 4/2010 | Cao et al. |
| 7,747,320 B1 | 6/2010 | Kroll |
| 7,783,354 B2 | 8/2010 | Gunderson |
| 7,974,690 B2 | 7/2011 | Kracker |
| 8,099,166 B2 | 1/2012 | Schuller |
| 8,200,330 B2 | 6/2012 | Kroll |
| 8,355,783 B2 | 1/2013 | Goetz et al. |
| 8,401,629 B2 | 3/2013 | Stadler et al. |
| 8,428,697 B2 | 4/2013 | Zhang et al. |
| 8,626,293 B2 | 1/2014 | Bornzin et al. |
| 8,738,111 B2 | 5/2014 | Sweeney et al. |
| 2002/0120307 A1 | 8/2002 | Jorgenson |
| 2005/0137636 A1 | 6/2005 | Gunderson et al. |
| 2006/0235476 A1 | 10/2006 | Gunderson |
| 2006/0264777 A1 | 11/2006 | Drew |
| 2007/0100407 A1 | 5/2007 | Armstrong |
| 2007/0293903 A1 | 12/2007 | Bohn |
| 2008/0161870 A1 | 7/2008 | Gunderson |
| 2009/0270938 A1 | 10/2009 | Pei |
| 2010/0023084 A1 | 1/2010 | Gunderson |
| 2010/0114222 A1 | 5/2010 | Gunderson |
| 2011/0009918 A1 | 1/2011 | Bornzin |
| 2011/0054558 A1 | 3/2011 | Gunderson |
| 2012/0109235 A1 | 5/2012 | Sheldon |
| 2012/0143278 A1 | 6/2012 | Ryu |
| 2012/0158089 A1 | 6/2012 | Bocek |
| 2013/0013038 A1 | 1/2013 | Miller |
| 2014/0276155 A1 | 9/2014 | Zhang |
| 2014/0277229 A1 | 9/2014 | Gunderson |

IDENTIFYING LEAD PROBLEMS USING AMPLITUDES OF FAR-FIELD CARDIAC EVENTS

FIELD OF THE DISCLOSURE

The disclosure relates generally to implantable medical systems that include an implantable medical device (IMD) coupled to one or more electrical stimulation leads and, more particularly, IMDs and methods for detecting a lead problems using amplitudes of far-field cardiac events.

BACKGROUND

Implantable medical systems that provide electrical stimulation therapy and/or sense physiological parameters of a patient typically include an implantable medical device (IMD) coupled to one or more electrical stimulation leads. IMDs may deliver therapy to or monitor conditions of a variety of organs, nerves, muscle or tissue, such as the heart, brain, stomach, spinal cord, pelvic floor, and the like. In the case of implantable cardiac systems, the IMD may be configured to provide electrical stimulation therapy to the heart and/or sense electrical activity of the heart via the electrical stimulation lead(s). One such IMD, the implantable cardioverter-defibrillator (ICD), may be capable of delivering both low voltage therapies and high voltage therapies in response to monitoring a cardiac rhythm and detecting a need for therapy.

Low voltage therapies may include bradycardia pacing, cardiac resynchronization therapy (CRT), and anti-tachycardia pacing (ATP). Low voltage therapies are typically delivered using low voltage pacing electrodes, e.g., tip or ring electrodes, together or in conjunction with the housing of the ICD, often referred to as the "CAN electrode" or a "housing electrode." Low voltage therapies may include pulses delivered at 5 volts (V) or less in amplitude. High voltage therapies, such as cardioversion or defibrillation shocks, are delivered in response to detecting ventricular tachycardia (VT) or ventricular fibrillation (VF). High voltage therapies are typically delivered using high voltage coil electrodes and the housing or CAN electrode. High voltage electrodes generally have a greater surface area than low voltage electrodes and deliver high energy shock pulses, typically in the range of at least 10 Joules and up to 35 Joules for transvenous systems and in the range of at least 65 Joules and up to 80 Joules for subcutaneous systems.

A single lead coupled to an ICD may carry multiple electrodes, which may include either or both high voltage and low voltage electrodes. Each electrode is electrically coupled to an electrically insulated conductor extending through the elongated lead body to facilitate electrical connection of each electrode to circuitry within the ICD. Lead problems can sometimes occur when an electrode, or the conductor to which it is electrically coupled, makes electrical contact with another conductor or electrode including the housing electrode. These lead problems may result in inappropriate sensing (e.g. oversensing) or in inadequate delivery of stimulation therapy.

SUMMARY

In general, the disclosure is directed to techniques for detecting lead problems, such as a short circuit condition, of an implantable medical electrical lead. An ICD operating in accordance with the techniques performs cardiac electrical signal analysis for detecting the short circuit conditions.

In one example, the disclosure provides an implantable medical system. The implantable medical system includes at least one medical electrical lead and an implantable medical device electrically coupled to the at least one medical electrical lead. The medical electrical lead includes a plurality of electrodes carried by the at least one medical electrical lead and a plurality of electrical conductors, each of the plurality of electrical conductors electrically connected to a respective one of the plurality of electrodes. The implantable medical device includes a housing at least partially formed of a conductive material, the conductive material forming a housing electrode, a sensing module electrically coupled to a near field (NF) sensing vector between a first pair of electrodes of the plurality of electrodes carried by the lead and located within a first chamber of a heart to obtain a NF cardiac electrical signal and electrically coupled to a far-field (FF) sensing vector between a second pair of electrodes, at least one of the second pair of electrodes being located outside the first heart chamber of the heart, to obtain a FF cardiac electrical signal, and a control module electrically coupled to the sensing module, wherein the control module detects a NF cardiac event in the NF cardiac electrical signal, determines an amplitude of a FF cardiac event in the FF cardiac electrical signal coincident the detected NF cardiac event, compares the amplitude of the coincident FF cardiac event to a threshold amplitude, and detects a short circuit condition on the FF sensing vector when the amplitude of the coincident FF cardiac event is less than the threshold amplitude.

In another example, the disclosure provides a method comprising obtaining a near-field (NF) cardiac electrical signal sensed via a NF sensing vector between a first pair of electrodes located within a first chamber of a heart and obtaining a far-field (FF) cardiac electrical signal sensed via a FF sensing vector between a second pair of electrodes, wherein at least one of the second pair of electrodes is located outside the first heart chamber of the heart. The method also includes detecting a NF cardiac event in the NF cardiac electrical signal and determining an amplitude of a FF cardiac event in the FF cardiac electrical signal coincident the detected NF cardiac event. The method further includes comparing the amplitude of the coincident FF cardiac event to a threshold amplitude and detecting a short circuit condition on the FF sensing vector when the amplitude of the coincident FF cardiac event is less than the threshold amplitude.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1:
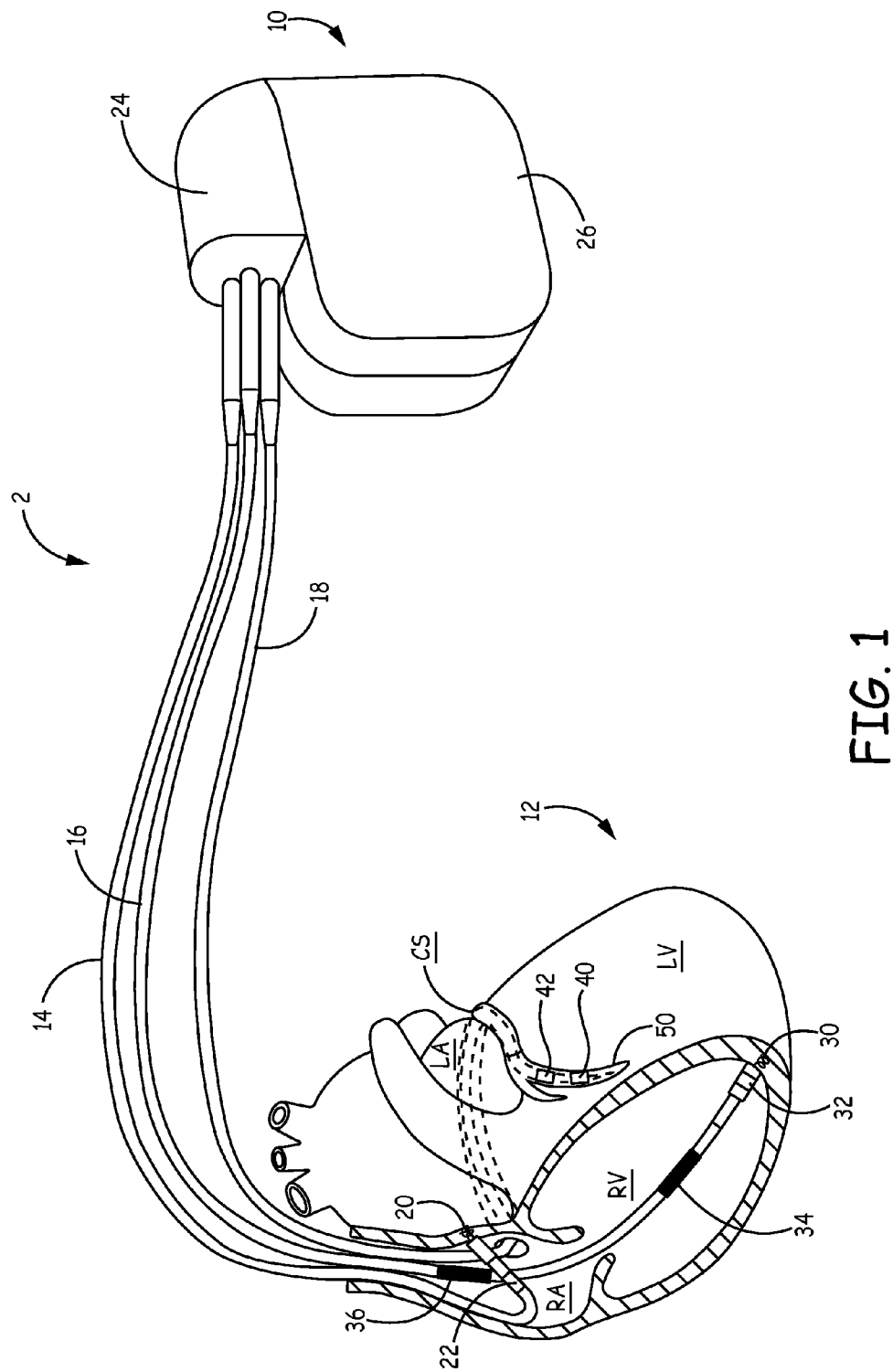
FIG. 1 is a schematic representation of an implantable medical system that includes an implantable medical device (IMD) coupled to a plurality of implantable electrical leads.

FIG. 1 is a schematic representation of an implantable medical system 2 that includes an implantable medical device (IMD) 10 coupled to implantable electrical leads 14, 16 and 18. IMD 10 of FIG. 1 is capable of delivering high voltage and low voltage therapies to heart 12 via leads 14, 16 and 18. Additionally, IMD 10 senses electrical signals of heart 12 via leads 14, 16 and 18.

IMD 10 may include a housing 26 that forms a hermetic seal that protects components of IMD 10. Housing 26 of IMD 10 may be formed of a conductive material, such as titanium or titanium alloy, that may function as a housing electrode (sometimes referred to as a CAN electrode). IMD 10 may also include a connector assembly 24 (also referred to as a connector block or header) that includes electrical feedthroughs through which mechanical and electrical connections are made between leads 14, 16 and 18 and electronic components included within the housing 26. As will be described in further detail herein, housing 26 may house one or more processors, memories, transmitters, receivers, sensors, sensing circuitry, therapy circuitry, power sources and other appropriate components. Housing 26 is configured to be implanted in a patient, such as a human patient.

Lead 14 extends from IMD 10 to the right atrium (labeled "RA" in FIG. 1) of heart 12. Lead 14 includes electrodes 20 and 22 along a distal portion of lead 14 for sensing cardiac electrical signals and delivering electrical stimulation (e.g., pacing pulses) in the right atrium. In addition, a housing electrode, also referred to as a CAN electrode, may be formed as part of the outer surface of housing 26 of IMD 10 and be used as an active electrode in combination with electrodes 20 and/or 22 to deliver the electrical stimulation or sense electrical signals in the right atrium. Lead 14 may have more or fewer electrodes. For example, lead 14 may include a defibrillation electrode, such as an SVC electrode.

Lead 16 extends from IMD 10 to the right ventricle (labeled "RV" in FIG. 1) of heart 12. Lead 16 includes electrodes 30 and 32 along a distal portion of lead 16 for sensing cardiac electrical signals and delivering low voltage electrical stimulation (e.g., pacing pulses) in the right ventricle. Lead 16 additionally includes coil electrodes 34 and 36, referred to herein as the right ventricle (RV) coil electrode 34 and the superior vena cava (SVC) coil electrode 36, for delivering high voltage cardioversion and defibrillation shocks in response to detecting a shockable tachyarrhythmia from sensed cardiac signals. In addition, the housing or CAN electrode formed on housing 26 may be used as an active electrode in combination with electrodes 30, 32, 34 and/or 36 during delivery of high voltage or low voltage electrical stimulation therapy and/or during sensing of cardiac electrical signals. Lead 16 may have more or fewer electrodes. For example, lead 16 may include only a RV coil electrode 34 instead of both RV coil electrode 34 and SVC electrode 36.

Lead 18 extends from IMD 10 into the coronary sinus. Lead 18 includes electrodes 40 and 42 for sensing cardiac signals and delivering electrical stimulation therapy (e.g., pacing pulses) along the left ventricle (labeled "LV" in FIG. 1). In some examples, lead 18 may additionally carry electrodes for positioning along the left atrium for sensing and stimulation along the left atrial chamber (labeled "LA" in FIG. 1). Moreover, lead 18 may carry additional electrodes positioned along the left ventricle, e.g., four electrodes. In addition, housing or CAN electrode formed on housing 26 may be used as an active electrode in combination with electrodes 40 and/or 42 to deliver the electrical stimulation therapy and/or sense cardiac electrical signals along the left ventricle.

Leads 14, 16 and 18 each include an elongated lead body having a proximal end that includes a connector configured to be connected to connector assembly 24 of IMD 10 and a distal portion that includes respective electrodes described above (e.g., electrodes 20, 22, 26, 30, 32, 34, 36, 40, and 42). The lead bodies of leads 14, 16 and 18 may be formed from a non-conductive material, including silicone, polyurethane, fluoropolymers, mixtures thereof, and other appropriate materials, and shaped to form one or more lumens within which the one or more conductors extend. However, the techniques are not limited to such constructions.

The elongated lead bodies of leads 14, 16 and 18 each contain a plurality of elongated electrical conductors (not illustrated) that extend within the lead body from connector assembly 24 at the proximal lead end to the electrodes located along the distal portion of the respective lead. The one or more elongated electrical conductors contained within the lead bodies of leads 14, 16 and 18 may engage with respective electrodes. In one example, each of electrodes 30, 32, 34 and 36 of lead 16 are electrically coupled to a respective conductor within the lead body. The conductors may electrically couple to circuitry, such as a therapy module or a sensing module, of IMD 10 via connections in connector assembly 24, including associated feedthroughs. The electrical conductors transmit therapy from a therapy module within IMD 10 to one or more of the electrodes and transmit sensed electrical signals from one or more of the electrodes to the sensing module within IMD 10.

The depicted positions in or about the right and left heart chambers are merely illustrative. Other leads and electrodes can be used instead of, or in combination with, any one or more of the depicted leads and electrodes shown in FIG. 1. Lead and electrode configurations are not limited to transvenous leads and intravenous or intracardiac electrodes as shown in FIG. 1. In some embodiments, an IMD system may include subcutaneous electrodes, which may be carried by an extravenous lead extending from IMD 10 subcutaneously outside the ribcage, or substernal electrodes, which may be carried by an extravenous lead having at least a distal end that extend underneath the sternum and/or ribcage (e.g., along the posterior side of the sternum).

IMD 10 is shown as a multi-chamber device capable of sensing and stimulation in three or all four heart chambers. It is understood that IMD 10 may be modified to operate as a single chamber device, e.g., with a lead positioned in the right ventricle only, or a dual chamber device, e.g., with a lead positioned in the right atrium and a lead positioned in the right ventricle. In general, IMD 10 may be embodied as any single, dual or multi-chamber device including lead and electrode systems. In other embodiments, IMD 10 may be a non-cardiac IMD configured to deliver therapy to and/or sense physiological parameters of other portions of the body. For example, IMD 10 may be a neuromodulation device configured to delivery electrical stimulation therapy to or sense electrical activity of the brain, spinal cord, pelvis, stomach, or other nerve, muscle or organ of the patient.

Figure 2:
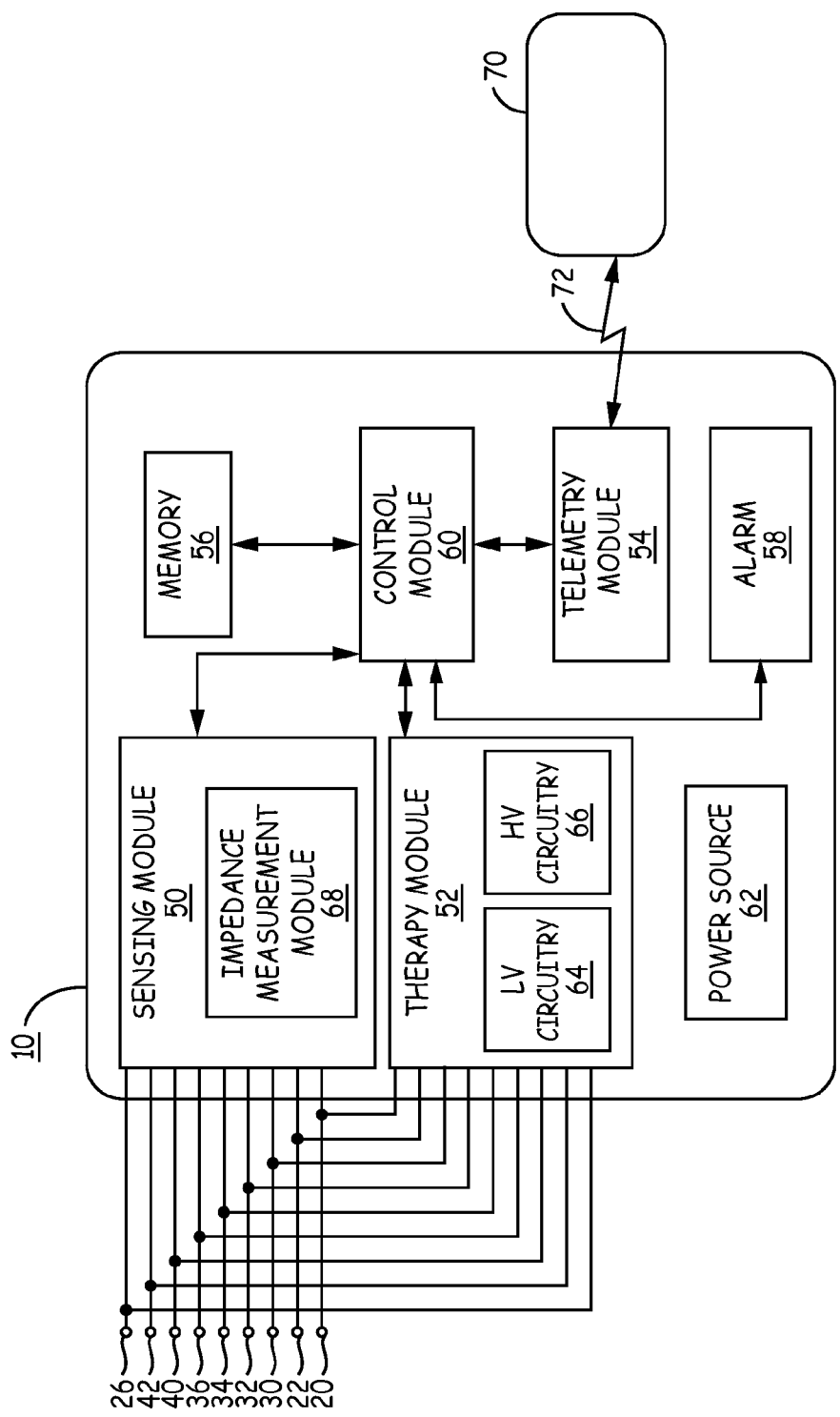
FIG. 2 is a functional block diagram of components of an example IMD.

FIG. 2 is a functional block diagram of the IMD 10 shown in FIG. 1 according to an illustrative embodiment. IMD 10 includes a sensing module 50, a therapy delivery module 52, a telemetry module 54, memory 56, alarm 58 and a control module 60. The various modules of IMD 10 may be powered by a power source 62. Additionally, the various components (including power source 62) of IMD 10 may be electrically connected to some or all of the other components via a data/address bus and/or one or more direct electrical connections. In other example, IMD 10 may include more or fewer components. The described modules may be implemented together on a common hardware component or separately as discrete but interoperable hardware or software components. Depiction of different features as modules is intended to highlight different functional aspects and does not necessarily imply that such modules must be realized by separate hardware or software components. Rather, functionality associated with one or more modules may be performed by separate hardware or software components, or integrated within common or separate hardware or software components.

Sensing module 50 may be selectively coupled to combinations of electrodes 20, 22, 30, 32, 34, 36, 40, 42 and housing electrode 26 (all shown in FIG. 1) for sensing cardiac electrical signals, such as cardiac electrogram (EGM) signals, via the conductors of leads 14, 16 and 18 and one or more electrical feedthroughs of connector block 24, or to the housing electrode via conductors internal to housing 26 of IMD 10. Sensing module 50 may include a switch module (not illustrated) to select which of the available electrodes are used to sense the cardiac electrical activity. The switch module may include a switch array, switch matrix, multiplexer, or any other type of switching device suitable to selectively couple electrodes to sensing module 50. In some examples, control module 60 selects the electrodes to function as sense electrodes, or the sensing vector, via the switch module within sensing module 50.

Sensing module 50 may include multiple sensing channels, each of which may be selectively coupled to respective combinations of electrodes 20, 22, 26, 30, 32, 34, 36, 40 and 42 to process electrical signals sensed via respective sensing vectors. Each sensing channel may include one or more analog components, digital components or a combination thereof. Each sensing channel of sensing module 50 may, for example, include one or more sense amplifiers, filters, rectifiers, threshold detectors, analog-to-digital converters (ADCs) or the like. Sensing module 50 may convert the sensed signals to digital form and provide the digital signals to control module 60 for processing or analysis. For example, each sensing channel may amplify signals from the sensing electrodes of its respective sensing vector and convert the amplified signals to multi-bit digital signals using an analog-to-digital converter (ADC). Sensing module 50 may compare the processed signals to a threshold to detect the existence of atrial or ventricular depolarizations and indicate the existence of the atrial depolarization (e.g., P-waves) or ventricular depolarizations (e.g., R-waves) to control module 60. Sensing module 50 may further include digital signal processing circuitry, e.g., filters, rectifiers, and the like, that process the signals to providing control module 60 with digitized EGM signals, which may be used to determine EGM signal features or for signal morphology analysis in some embodiments.

In one example, the different sensing channels may be coupled to various electrode combinations for providing both near field (NF) sensing vectors and far field (FF) sensing vectors. As used herein, a FF sensing vector is an electrode vector that senses electrical signals using at least one electrode located outside the heart chamber for which signals are being sensed, in either a different heart chamber or even outside the heart. For example, a FF sensing vector for sensing ventricular cardiac signals may be formed using coil electrode 34 and housing electrode 26. A FF signal is a signal that is obtained using a FF sensing vector. A NF sensing vector is an electrode vector that includes a pair of sensing electrodes that are both located in the same heart chamber for which events are being sensed. For example, a NF sensing vector for sensing ventricular cardiac signals may be formed between electrode 30 and electrode 32. A NF signal is a signal that is obtained using a NF sensing vector.

Control module 60 may process the signals from sensing module 50 to monitor electrical activity of heart 12. In one example, control module 60 may monitor the electrical activity of the heart 12 using the NF cardiac electrical signal. Control module 60 may store, in memory 56, cardiac electrical signals obtained by sensing module 50 including any detected events (e.g., P-waves and/or R-waves), generated EGM waveforms, marker channel data or other data derived based on the sensed signals. Control module 60 may analyze the detected events, EGM waveforms and/or marker channel data to detect tachycardia, bradycardia, or other abnormal cardiac rhythms. In response to detecting an abnormal cardiac rhythm, control module 60 may control therapy module 52 to deliver the desired therapy to treat the abnormal cardiac rhythm, e.g., defibrillation shock, cardioversion shock, anti-tachycardia pacing (ATP), post-shock pacing, or bradycardia pacing in accordance with programmed therapies stored in memory 56.

Therapy delivery module 52 is selectively coupled to combinations of electrodes 20, 22, 26, 30, 32, 34, 36, 40, and 42 for delivering electrical stimulation therapy to the patient's heart. In some embodiments, therapy delivery module 52 may include low voltage (LV) therapy circuitry 64 including a pulse generator for generating and delivering low voltage pacing pulses during bradycardia pacing, cardiac resynchronization therapy (CRT), post-shock pacing and/or anti-tachycardia pacing (ATP). Control module 60 controls LV therapy circuitry 64 to deliver pacing pulses according to programmed control parameters using electrodes 20, 22, 30, 32, 40, 42 and/or housing electrode 26 for example. Electrodes 20, 22, 30 32, 40 and 42 are generally referred to as "low voltage" electrodes because they are normally used for delivering relatively low voltage therapies such as pacing therapies as compared to the high voltage therapies, e.g., cardioversion and defibrillation therapies, delivered by high voltage coil electrodes 32 and 34. However, in some instances, low voltage electrodes 20, 22, 30, 32 40 and 42 may be used for delivering a high voltage therapy.

Therapy delivery module 52 also includes high voltage (HV) therapy delivery circuitry 66 for generating and delivering high voltage cardioversion and defibrillation shock pulses. HV therapy delivery circuitry 66 includes HV capacitors that are charged in response to detecting a shockable cardiac rhythm, e.g., VT or VF. After determining the HV capacitors have reached a targeted voltage, according to a programmed shock energy, HV therapy delivery 130 delivers a shock pulse via selected HV electrodes, e.g., coil electrodes 34, 36 and/or housing electrode 26.

Therapy module 52 may include a switch module to select which of the available electrodes are used to deliver electrical stimulation therapy. The switch module may include a switch array, switch matrix, multiplexer, or any other type of switching device suitable to selectively couple electrodes to therapy module 52. In some examples, control module 60 selects the electrodes to function as therapy electrodes, or the therapy vector, via the switch module within therapy module 52. In some instances, the same switch module may be used by for selecting the electrode vectors for sensing module 50 and therapy module 52.

Problems with one or more of leads 14, 16 and 18 may result in inappropriate sensing or ineffective delivery of therapy. For example, insulation breaches of the lead body of lead 16 (or other lead) or fractures of conductors connected to electrodes 34 or 36 (or other electrodes) may impact the energy needed to defibrillate the heart. As such, IMD 10 may include circuitry and algorithms to monitor for lead problems, such as short circuit conditions caused by insulation breaches and fractures of conductors. As will be described in further detail herein, a short circuit between a lead conductor and housing electrode 26, another electrode, and/or another one of the lead conductors may cause FF cardiac events of the FF cardiac electrical signal that are coincident with detected NF cardiac events in the NF cardiac electrical signal to have a significantly reduced amplitude after such a condition occurs.

Therefore, control module 60 may be configured to obtain the FF cardiac electrical signal sensed via the FF sensing vector and determine amplitudes of FF cardiac events in the FF cardiac electrical signal that are coincident to detected NF cardiac events. A FF cardiac event in the FF cardiac electrical signal that is coincident to a detected NF cardiac event will be referred to herein as a coincident FF cardiac event or FF cardiac event. The coincident FF cardiac event may be detected by analyzing a window of time in the FF cardiac signal centered or otherwise placed based on the detection of the NF cardiac event on the NF cardiac electrical signal. For example, at the time of a sensed or paced event detected on the NF cardiac electrical signal, control module may analyze a 100 ms window on the FF cardiac electrical signal to determine the EGM voltage amplitude within the 100 ms window. The control module 60 may calculate the EGM voltage amplitude as a peak-peak amplitude between the maximum and minimum EGM voltage values during the window. The 100 ms window may be +50 ms and −50 ms of the time at which the NF cardiac event is detected. In other examples, the window may be larger or smaller than 100 ms. Other example techniques for detecting FF cardiac events in an FF cardiac electrical signal are described in U.S. Pat. No. 7,567,835 (Gunderson et al.), which is incorporated herein by reference in its entirety.

Control module 60 determines whether there is a significant amplitude reduction in the current coincident FF cardiac event. Control module 60 may, for example, compare the amplitude the current FF cardiac event to an amplitude threshold and determine a significant reduction in amplitude exists if the amplitude of current FF cardiac event is less than the amplitude threshold. The amplitude threshold may be a value determined by control module 60 or configured by a physician or other health care professional. Control module 60 may, in one example, determine the value of the amplitude threshold based on the amplitude of a previous FF cardiac event or based on the amplitudes of more than one previous FF cardiac events. In one example, the amplitude threshold may be equal to a percentage of the amplitude of one or more previous FF cardiac events with matching morphology. The percentage may be any percentage less than 60% in one example. In another example, the amplitude threshold may be a mean (e.g., average) of a number of previous FF cardiac events, a median value of the number of previous FF cardiac events, or a mode of the number of previous FF cardiac events. In a further example, the amplitude threshold may be a selected one of the previous number of FF cardiac events (e.g., the amplitude of the most recent FF cardiac event, the smallest FF cardiac event of the subset of FF cardiac events or the largest FF cardiac event of the subset of FF cardiac events).

In some instances, control module 60 may detect a lead problem (e.g., a short circuit condition) on the FF sensing vector when there is a significant amplitude reduction, e.g., when the amplitude of the coincident FF cardiac event is less than the threshold amplitude. In response to detecting the lead problem, control module 60 may generate an alert. In one example, control module 60 may generate the alert by setting a flag or other warning that is displayed to physician during a next follow up visit and/or transmitting an alert message to the physician, hospital, nurse, clinic, patient, or other entity via a monitoring device and/or network (such as the Medtronic Carelink® Network). In other embodiments, control module 60 may cause an external device (e.g., device 70) to initiate a call to an emergency number directly.

In another example, IMD 10 may optionally be equipped with alarm circuitry 58 for notifying the patient or other responder that a patient alert condition has been detected by IMD 10. In one embodiment, the alarm 58 may emit an audible tone or notification and/or tactile notification (e.g., vibration) to alert the patient or a responder that immediate medical attention is required. For example, when a lead-related problem is detected, such as a short circuit involving HV coil electrodes 34 and 36 or their respective conductors, alarm 58 may be used to notify the patient, a caregiver or other responder that medical attention is required.

In some instances, control module 60 uses other information in addition to the significant drop in amplitude of the FF cardiac event to detect the lead problem. For example, in response to the amplitude of the coincident FF cardiac event being less than the threshold amplitude, control module 60 may analyze a morphology of the portion of the FF cardiac electrical signal including the coincident FF cardiac event to determine whether the short circuit condition exists. Control module 60 may compare characteristics of the portion of the FF cardiac electrical signal that includes the FF cardiac event to a morphology template stored in memory 82 for the respective sensing vector. The morphology analysis may, for example, determine a morphology matching score or other metric of the correlation between the portion of the FF cardiac electrical signal having the FF cardiac event of interest and the morphology template.

The morphology template may represent a cardiac electrical signal (or an average of a plurality of cardiac electrical signals) that includes a cardiac event during a normal cardiac rhythm (e.g., during normal sinus tachycardia). In another example, features of a cardiac electrical signal or an averaged cardiac electrical signal may be stored as the template. Stored features may pertain to the Q-wave, R-wave, T-wave, QRS complex, or any desired portion of a cardiac electrical signal and/or cardiac event within the signal. Features may include, with no limitation intended, waveform area, normalized amplitude(s), slope(s), frequency content, signal width, number of peaks, timing sequence of maximum amplitude points and/or maximum slope points, or a combination thereof. In another example, template wavelet coefficients are generated using a wavelet transform and stored as the template. In some instances, the morphology comparisons are amplitude independent. Methods for generating and updating a morphology template and making template comparison performed by ICD 10 may include techniques generally disclosed in U.S. Pat. No. 6,745,068 (Koyrakh, et al.), U.S. Pat. No. 7,706,869 (Cao, et al.), and U.S. Pat. No. 8,428,697 (Zhang, et al.), all of which are incorporated herein by reference in their entirety.

Numerous methods may be used to determine a morphology matching score that indicates the similarity or correlation between an FF cardiac electrical signal during an unknown rhythm and a morphology template obtained during sinus rhythm. In one example, determining a morphology matching score may include determining a waveform area difference between the FF cardiac electrical signal received from the selected sensing vectors during an unknown cardiac rhythm and morphology template stored for the selected sensing vectors. A normalized area waveform difference may be determined as generally disclosed in U.S. Pat. Pub. No. 2014/0276155 (Zhang et al.), hereby incorporated herein by reference in its entirety. A wavelet transform method as generally disclosed in U.S. Pat. No. 6,393,316 (Gillberg et al.), hereby incorporated herein by reference in its entirety, is another example of a morphology matching method that may be implemented in the techniques disclosed herein. Other morphology matching methods may be implemented by control module 60 which compare the wave shape, slopes, inflection time points, number of peaks, or other features of the ECG signal, particularly of the R-wave or QRS portion of the ECG signal.

In response to determining that the morphology of the portion of FF cardiac electrical signal matches the morphology template (e.g., a matching score is greater than or equal to a threshold score), control module 60 may detect the presence of a short circuit condition on the FF sensing vector. When the morphology of the portion of FF cardiac electrical signal does not match the morphology template (e.g., a matching score is less than the threshold score), control module 60 continues to analyze the amplitudes of subsequent FF cardiac events coincident with detected NF cardiac events.

In other instances, control module 60 determines whether the short circuit condition or other lead-related problem exists based on analysis of the amplitude of the coincident FF cardiac events and impedance measurements of the FF electrode vector used to sense the FF cardiac events. For example, control module 60 may analyze one or more impedance measurements of the FF sensing vector in response to the amplitude of the coincident FF cardiac event being less than the threshold amplitude to determine whether the short circuit condition or other lead-related problem exists. To this end, IMD 10 may include an impedance measurement module 68 that measures an impedance of the electrode vector of interest, in this case the FF electrode vector used to sense the FF electrical signal. Control module 60 may control impedance measurement module 68 to measure impedances after detecting the significant amplitude drop of the coincident FF cardiac event.

Control module 60 may perform an impedance measurement by controlling delivery, from LV therapy circuitry 64 or other signal generator, of a voltage pulse between first and second electrodes of the electrode vector of interest. Impedance measurement module 68 may measure a resulting current, and control module 60 may calculate a resistance based upon the voltage amplitude of the pulse and the measured amplitude of the resulting current. In other examples, control module 60 may perform an impedance measurement by controlling delivery, from LV therapy circuitry 64 or other signal generator, of a current pulse between first and second electrodes of the electrode vector of interest, impedance measurement module 68 may measure a resulting voltage, and control module 60 may calculate a resistance based upon the current amplitude of the pulse and the measured amplitude of the resulting voltage. Impedance measurement module 68 may include circuitry for measuring amplitudes of resulting currents or voltages, such as sample and hold circuitry.

The drive signal is generally a low voltage signal. The drive signal may be a sub-threshold electrical stimulation pulse. In certain cases, IMD 10 may collect impedance values that include both a resistive and a reactive (i.e., phase) component. In such cases, IMD 10 may measure impedance during delivery of a sinusoidal or other time varying signal by LV therapy circuitry 64 or other signal generator, for example. Thus, as used herein, the term "impedance" is used in a broad sense to indicate any collected, measured, and/or calculated value that may include one or both of resistive and reactive components.

Control module 60 may utilize the combination of the significant drop in amplitude on the electrode vector and the one or more impedance measurements to detect potential lead problems, such as short circuit conditions. For example, control module 60 may determine that a short circuit condition exists on the FF electrode vector when the coincident FF events have a significant amplitude reduction and one or more impedance measurements taken on the FF electrode vector after the reduction in amplitude of FF events is less than a normal impedance threshold.

In further instances, control module 60 determine whether the short circuit condition or other lead-related problem exists based on analysis of the amplitude of the coincident FF cardiac events, morphology of the coincident FF cardiac events and impedance measurements of the FF electrode vector. For example, control module 60 may detect a short circuit condition in response to identifying a significant amplitude reduction in at least one coincident FF cardiac event having a morphology that matches the morphology template and at least one impedance measurement taken after the coincident FF cardiac event is less than the impedance threshold.

Control module 60 may periodically analyze the FF electrical signals to monitor for a significant drop in the amplitude of the coincident FF cardiac events indicative of a possible lead problem. For example, control module 60 may periodically analyze the FF electrical signals, e.g., hourly, several times per day, daily, weekly or other periodic interval, to monitor for a significant drop in the amplitude of the FF cardiac events indicative of a possible lead problem. In one particular example, control module 60 may periodically analyze a 10 second segment of the FF electrical signal every hour. The sensing module may include a first sensing channel having a first amplifier that obtains the NF cardiac electrical signal via the NF sensing vector and a second sensing channel having a second sensing amplifier that obtains the FF cardiac electrical signal via the FF sensing vector. T second sensing amplifier may be periodically powered on to obtain the FF cardiac electrical signal via the FF sensing vector. Alternatively, control module 60 may continually analyze the FF electrical signals to monitor for a significant drop in the amplitude of the FF cardiac events indicative of a possible lead problem. In other embodiments, however, that identification of a short circuit condition may be performed during post processing.

In other instances, control module 60 may analyze the FF electrical signals to monitor for a significant drop in the amplitude of the coincident FF cardiac events in response to a triggering event. In one example, the triggering event may be one or more abnormal impedance measurements. Control module 60 may measure one or more impedances of the FF electrode vector (as described in further detail above) and cause IMD 10 to begin sensing and analyzing the FF cardiac electrical signal for significant impedance drops in accordance with the various techniques described herein in response to the impedance being out of range (e.g., less than a threshold impedance). Control module 60 may, for example, be configured to periodically measure an impedance of the FF electrode vector, e.g., daily, weekly, monthly, or the like. Alternatively, control module 50 may periodically measure the impedance of the FF electrode vector in response to a trigger, such as those described below.

In another example, IMD 10 may include one or more physiological sensors (e.g., pressure sensors, accelerometers, flow sensors, blood chemistry sensors, activity sensors or other physiological sensors known for use with implantable cardiac stimulation devices) and trigger analysis of the FF electrical signals and/or the impedance measurements based on the output of the physiological signals. Changes in lead motion, flexion or pressure due to changes in patient body motion, cardiac motion, respiratory motion, or body posture may put a unique stress on a medical electrical lead, such as any of leads 14, 16 or 18 shown in FIG. 1 or other subcutaneous, submuscular or substernal leads that may be present in other ICD systems. The change in lead motion, flexion or pressure may result in a short circuit condition that is discontinuous, i.e., present only during the unique stress or more likely to present itself during the unique stress. The likelihood of promptly detecting an intermittent short circuit condition is reduced when the short circuit condition is dependent on a motion or posture of the patient's body since the condition may not be detected during routine lead impedance measurements or other lead integrity tests performed on a scheduled basis.

Accordingly, analysis of the FF electrical signal may be triggered to occur when a condition is detected that is likely to impose unique stress on the lead(s) making the presence of an intermittent short circuit condition manifest. A physiological signal is sensed from a physiological sensor may be correlated to a motion of the patient, which may be cardiac, respiratory or body motion and may be used to trigger the analysis of the FF electrical signal. The motion may be any indication that cardiac, respiratory, or patient body motion including body posture, have changed or increased. Example of motion metrics include, with no limitation intended, heart rate, respiration rate, patient activity, systolic blood pressure (ventricular or arterial), and body posture.

The functions attributed to the various modules herein may be embodied as software, firmware, hardware or any combination thereof. Memory 56 may store computer-readable instructions that, when executed by any of the modules, cause the modules and/or IMD 10 to perform various functions attributed throughout this disclosure to them. The computer-readable instructions may be encoded within memory 56. Memory 56 may comprise non-transitory computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media, with the sole exception being a transitory propagating signal.

Control module 60 may, for example, be embodied as a processor including any one or more of a microprocessor, a digital signal processor (DSP), an application specific integrated circuit (ASIC), a field-programmable gate array (FPGA), or equivalent discrete or integrated logic circuitry. The processor may retrieve the computer-readable instructions from memory 56 and execute those instructions to cause the processor to perform the functions attributed to it. In some examples, control module 60 may include multiple components, such as any combination of one or more microprocessors, one or more control modules, one or more DSPs, one or more ASICs, or one or more FPGAs, as well as other discrete or integrated logic circuitry.

Telemetry module 54 is used for transmitting data accumulated by IMD 10 wirelessly to an external device 70, such as a programmer, home monitor, or handheld device. Examples of communication techniques used by IMD 10 include low frequency or radiofrequency (RF) telemetry, which may be an RF link established via Bluetooth, WiFi, MICS, or other proprietary or non-proprietary communication protocol. IMD 10 may receive programming commands and algorithms from external device 70 via telemetry link 72 with telemetry module 54. For example, external device 70 may be used to program tachyarrhythmia detection parameters used by control module 60. Telemetry module 54 may be controlled by control module 60 for delivering a patient or clinician alert or notification to external device 70 in response to detecting a short circuit condition.

Figure 3A:
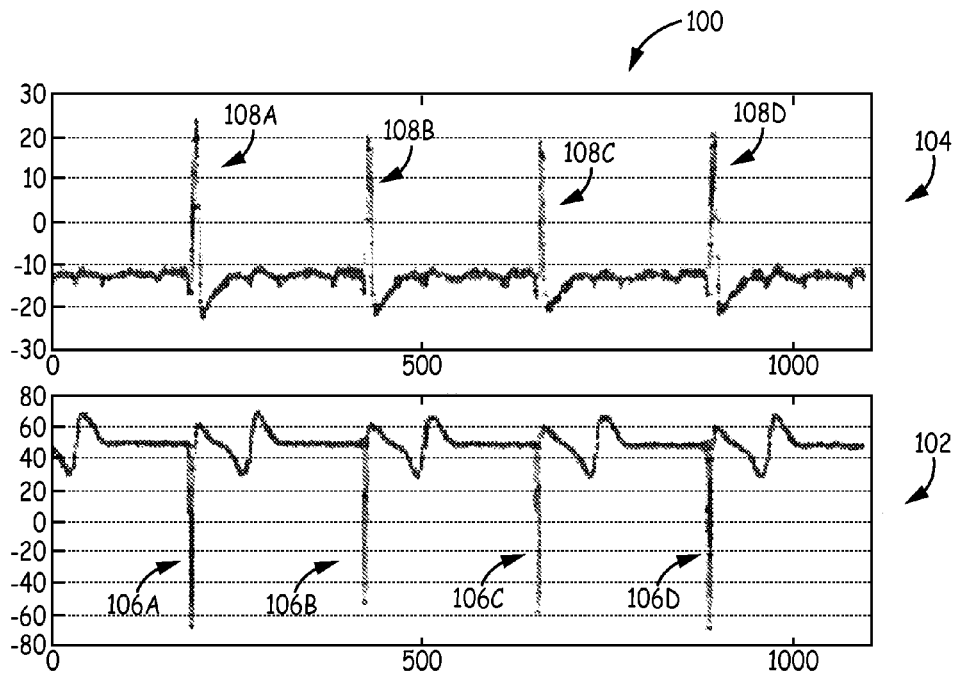
FIG. 3A shows an example EGM recording that illustrate a NF cardiac electrical signal and a FF cardiac electrical signal sensed when no lead problems exist.
Figure 3B:
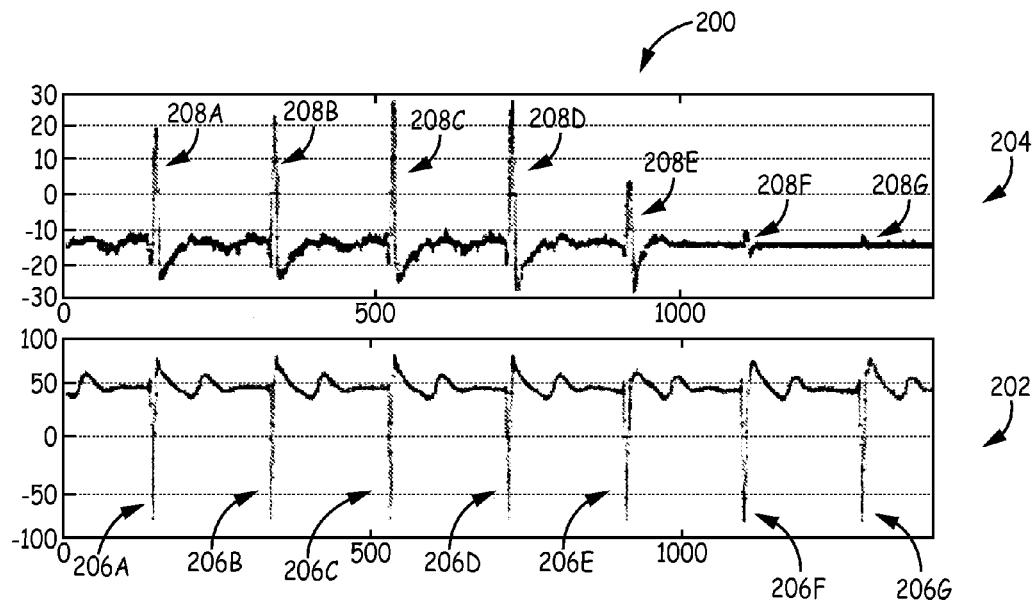
FIG. 3B shows an example EGM recording that illustrate a NF cardiac electrical signal and a FF cardiac electrical signal sensed when a short circuit condition exists on the FF sensing vector.
Figure 3C:
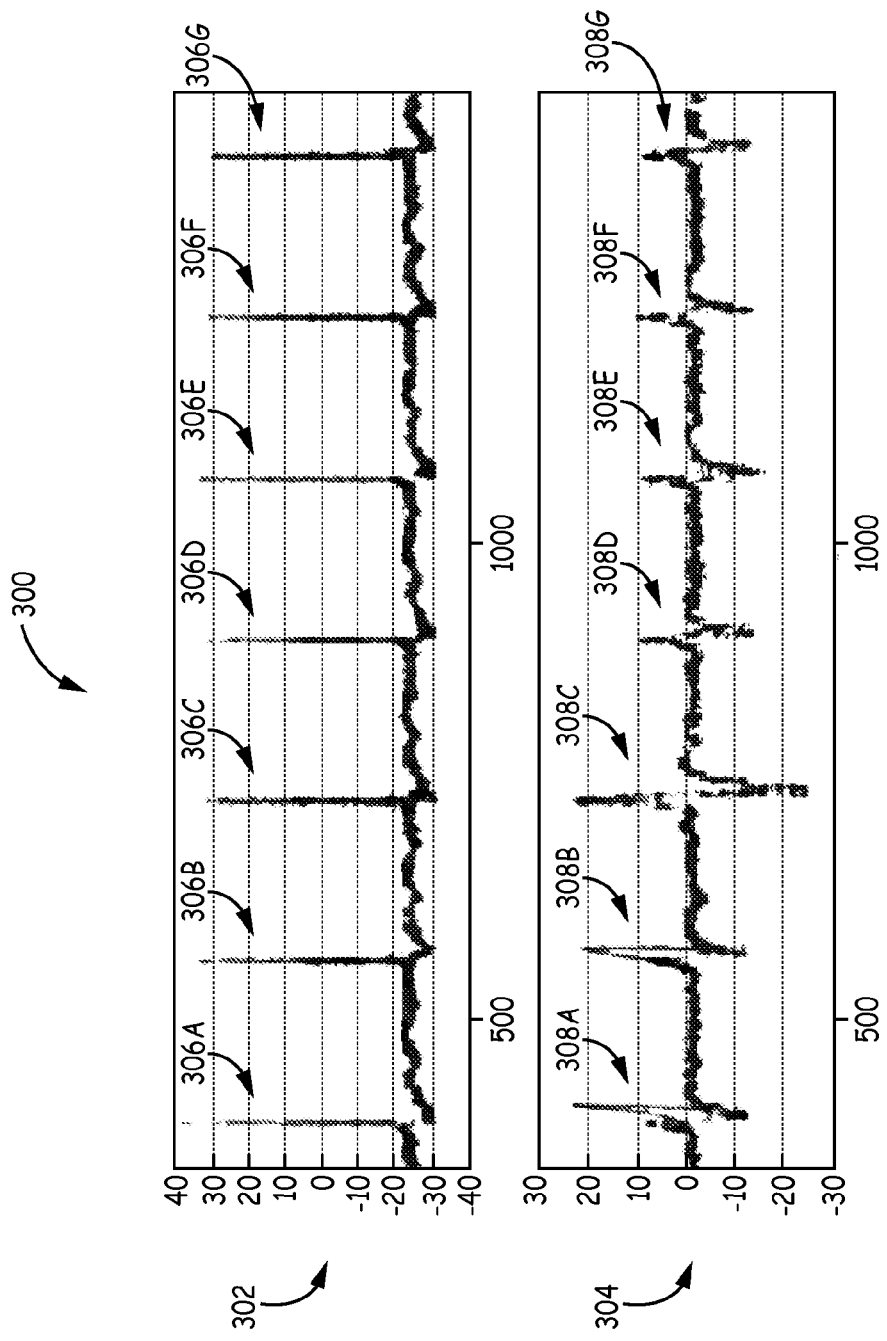
FIG. 3C shows another example EGM recording that illustrates another NF cardiac electrical signal and a FF cardiac electrical signal sensed when a short circuit condition exists on the FF sensing vector.

FIGS. 3A-C show exemplary FF and NF electrical signals sensed using FF and NF sensing vectors, respectively. FIG. 3A shows an example EGM recording 100 that illustrate a NF cardiac electrical signal 102 and a FF cardiac electrical signal 104 sensed when no lead problems exist. NF cardiac electrical signal 102 is sensed using a NF sensing vector, such as between electrodes 30 and 32 of lead 16. FF cardiac electrical signal 104 is sensed using a FF sensing vector, such as between coil electrode 34 of lead 16 and housing electrode 26. However, other NF and FF sensing vectors may be used to obtain NF and FF cardiac electrical signals, respectively.

As described above, NF cardiac electrical signal 102 is generally used to detect cardiac events within the chamber of interest (e.g., the ventricle in the example above) while the FF cardiac electrical signal 104 may be analyzed by control module 60 to monitor for any lead-related issues. In the NF cardiac electrical signal 102, four NF ventricular events 106A-D are detected. Control module analyzes the FF cardiac electrical signal 104 to detect coincident FF ventricular events 108A-D, e.g., using the FF event detection techniques described above. Each of the FF ventricular events 108 correspond with a respective NF ventricular event 106. In FF cardiac electrical signal 104 of FIG. 3A, the amplitude of ventricular events 108A-D maintain a relatively constant amplitude and therefore are not indicative of any lead problem.

FIG. 3B shows an example EGM recording 200 that illustrate a NF cardiac electrical signal 202 and a FF cardiac electrical signal 204 sensed when a short circuit condition exists on the FF sensing vector. In the NF cardiac electrical signal 202, seven NF ventricular events 206A-G are detected. Control module analyzes the FF cardiac electrical signal 204 to detect coincident FF ventricular events 208A-G, e.g., using the FF event detection techniques described above. Unlike FF cardiac electrical signal 104 of FIG. 3A, FF cardiac electrical signal 204 illustrates a significant drop in amplitude of the FF ventricular events after FF ventricular event 208D. In the illustrated example, the amplitude of coincident FF ventricular event 208E is only approximately half of the amplitude of coincident FF ventricular event 208D. The amplitudes of coincident FF ventricular events 208F and 208G drop even further and are approximately zero.

FIG. 3C shows another example EGM recording 300 that illustrates another NF cardiac electrical signal 302 and a FF cardiac electrical signal 304 sensed when a short circuit condition exists on the FF sensing vector. In the NF cardiac electrical signal 302, seven NF ventricular events 306A-G are detected. Control module analyzes the FF cardiac electrical signal 304 to detect coincident FF ventricular events 308A-G, e.g., using the FF event detection techniques described above. Like FF cardiac electrical signal 204 of FIG. 3B, there is a significant drop in amplitude of the coincident FF ventricular events after coincident FF ventricular event 308C. In the illustrated example, the amplitudes of coincident FF ventricular events 308D-G are approximately half of the amplitude of FF ventricular event 208C.

As described briefly above, such a significant decrease in amplitude of the coincident FF ventricular events may be indicative of a lead problem, e.g., a short circuit on the conductor connected to one of the electrodes of the FF electrode vector. In accordance with the techniques described herein, control module 60 is configured to analyze the amplitudes of the coincident FF cardiac events (e.g., R-waves) on the FF cardiac electrical and determine that a potential lead-related issue exists when there is a significant drop in the amplitude of the FF cardiac events in the FF cardiac electrical that correspond with the NF cardiac events of the NF cardiac electrical. Additional confirmation assessments may be made, such as monitoring for a corresponding drop in impedance on the electrode vector used to measure the FF cardiac electrical and/or a matching morphology.

Figure 4:
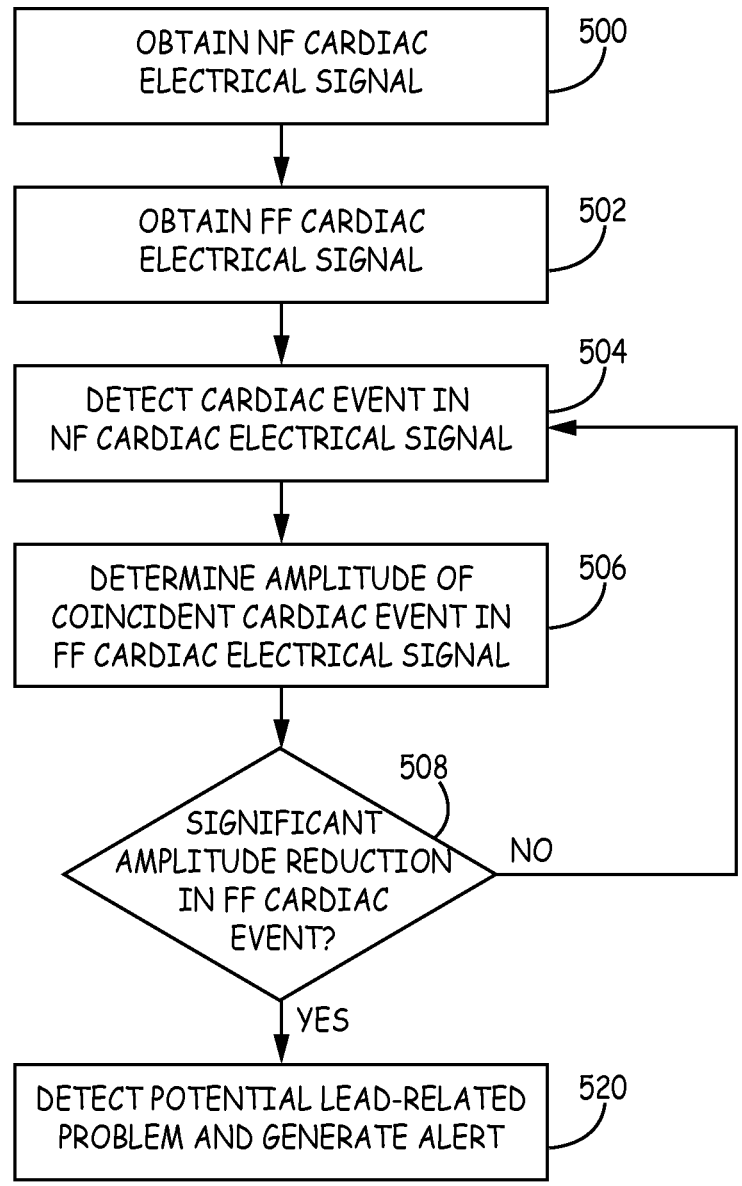
FIG. 4 is a flow diagram illustrating example operation of an IMD monitoring cardiac electrical signals to identify lead-related problems.

FIG. 4 is a flow diagram illustrating example operation of an IMD, such as IMD 10, monitoring cardiac electrical signals to identify lead-related problems. However, the techniques described with respect to FIG. 4 may be performed by an external device doing post processing of sensed cardiac electrical signals.

Initially, control module 60 obtains a NF cardiac electrical signal sensed using a NF sensing vector between a pair of electrodes located in the same heart chamber for which events are being sensed (500). Control module 60 also obtains a FF cardiac electrical signal sensed using a FF sensing vector between at least one electrode located outside the heart chamber for which events are being sensed, in either a different heart chamber or even outside the heart (502). In one example, the FF cardiac electrical signal may be sensed using a FF sensing vector between coil electrode 34 of lead 16 and housing electrode 26 and the NF cardiac electrical signal may be sensed using a NF sensing vector between electrode 30 and electrode 32 of lead 16. Other FF sensing vectors and NF sensing vectors may be utilized without departing from the scope of the disclosure.

Control module 60 may obtain the NF and FF cardiac electrical signals from memory 56. In other words, the NF and FF cardiac electrical signals may be previously stored in memory 56 and retrieved by control module 60 for analysis. In other instances, control module 60 may obtain the NF and FF cardiac electrical signals directly from sensing module 50 such that the signals are processed in more of real-time fashion or only slightly delayed fashion. As described in detail above, FF cardiac electrical may be sensed continuously, periodically, or in response to a triggering event.

Control module 60 (or sensing module 106) detects a cardiac event (e.g., an R-wave event) in the NF cardiac electrical signal (504). For example, cardiac events are detected in the NF cardiac electrical signal each time the amplitude of the sensed NF cardiac electrical signal exceeds a sensing threshold associated with the sensing channel. Control module 60 determines the amplitude of a cardiac event in the FF cardiac electrical signal coincident with the detected cardiac events in the NF cardiac electrical signal (506). Control module 60 may, in one example, determine the amplitude of the coincident FF cardiac events by analyzing a window of time in the FF cardiac signal centered or otherwise placed based on the detection of the NF cardiac event as described in more detail above.

Control module 60 determines whether there is a significant amplitude reduction in the coincident FF cardiac event (508). Control module 60 may compare the amplitude of the coincident FF cardiac event to an amplitude threshold and determine a significant amplitude reduction exists if the amplitude of coincident FF cardiac event is less than the amplitude threshold. The amplitude threshold may be a value determined by control module 60 or configured by a physician as described in detail above. When control module 60 determines that there is not a significant amplitude reduction in the coincident FF cardiac event ("NO" branch of block 508), control module 60 (possibly in conjunction with sensing module 106) detects a next NF cardiac event, determines the amplitude of the coincident FF cardiac event in the FF cardiac electrical signal, and determines whether there is a significant amplitude reduction in the coincident FF cardiac event (504, 506, and 508).

When control module 60 determines that there is a significant amplitude reduction in the coincident FF cardiac event ("YES" branch of block 508), control module 60 may detect a potential lead-related problem (e.g., short-circuit of conductor of the FF sensing vector) and generate an alert (510). The alert may be an audible or tactile (e.g., vibration) to notify the patient of the potential issue. Alternatively, the alert may be a flag or other warning that is displayed to physician during a next follow up visit and/or transmitted by IMD 10 to the physician via a monitoring device and/or network (such as the Medtronic Carelink® Network).

Figure 5:
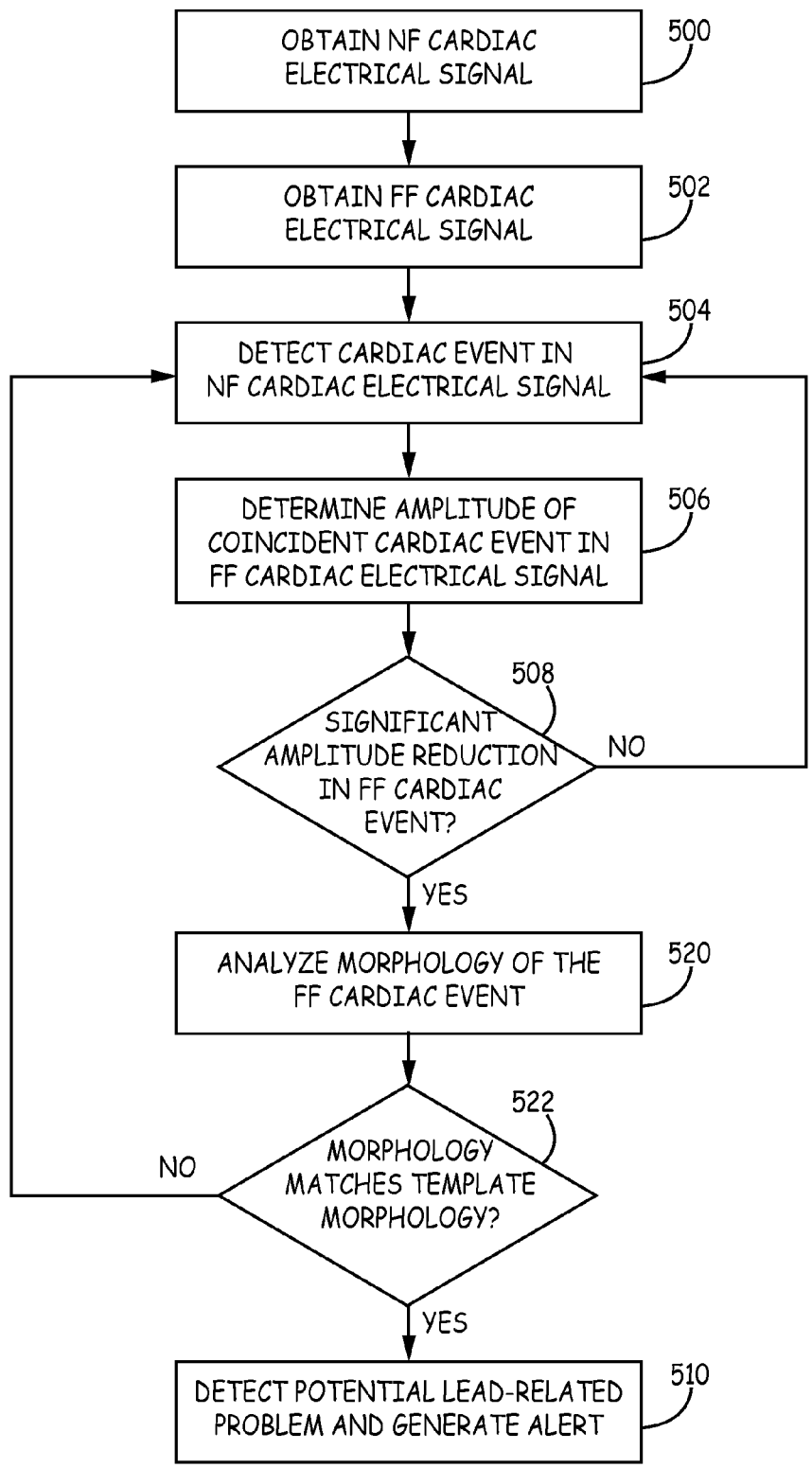
FIG. 5 is a flow diagram illustrating example operation of an IMD monitoring cardiac electrical signals to identify lead-related problems.

FIG. 5 is a flow diagram illustrating example operation of an IMD, such as IMD 10, monitoring cardiac electrical signals to identify lead-related problems. However, the techniques described with respect to FIG. 5 may be performed by an external device doing post processing of sensed cardiac electrical signals. The steps or operations performed in blocks 500, 502, 504, 506, 508, and 510 are the same as described above with respect to FIG. 4. As such, the repetitive description of those steps will not be repeated here, but are incorporated from above.

Control module 60 obtains a NF cardiac electrical signal sensed using a NF sensing vector between a pair of electrodes located in the same heart chamber for which events are being sensed (500). Control module 60 also obtains a FF cardiac electrical signal sensed using a FF sensing vector between at least one electrode located outside the heart chamber for which events are being sensed, in either a different heart chamber or even outside the heart (502). Control module 60 (or sensing module 106) detects a cardiac event (e.g., an R-wave event) in the NF cardiac electrical signal (504). Control module 60 determines the amplitude of coincident FF cardiac events in the FF cardiac electrical signal (506).

Control module 60 determines whether there is a significant amplitude reduction in the coincident FF cardiac event (508). When control module 60 determines that there is not a significant amplitude reduction in the coincident FF cardiac event ("NO" branch of block 508), control module 60 (possibly in conjunction with sensing module 106) detects a next NF cardiac event (504). When control module 60 determines that there is a significant amplitude reduction in the coincident FF cardiac event ("YES" branch of block 508), control module 60 analyzes a morphology of the FF cardiac electrical signal that includes the coincident FF cardiac event (520). Morphology analysis performed by control module 60 includes comparing the portion of the FF cardiac electrical signal that includes the coincident FF cardiac event to a morphology template stored in memory 82 for the respective sensing vector. The morphology analysis may, for example, determine a morphology matching score or other metric of the correlation between an ECG signal received by sensing module 50 during an unknown heart rhythm and a template generated during a known sinus rhythm and stored in memory 56. Numerous methods for analyzing the morphology of cardiac events to determine the similarity or correlation between an ECG signal during an unknown rhythm and a template obtained during sinus rhythm are described above with respect to FIG. 2.

When control module 60 determines that the morphology of the FF cardiac electrical signal that includes the coincident FF cardiac event matches the morphology template ("YES" branch of block 522), control module 60 detects a potential lead-related problem (e.g., short-circuit of a conductor of the FF sensing vector) and generates an alert (510). When control module 60 determines that the morphology of the FF cardiac electrical signal that includes the coincident FF cardiac event does not match the morphology template ("NO" branch of block 522), control module 60 (possibly in conjunction with sensing module 106) detects a next NF cardiac event, determines the amplitude of the coincident FF cardiac event, and determines whether there is a significant amplitude reduction in the coincident FF cardiac event (504, 506, and 508).

In other instances, steps 520 and 522 may occur before steps 506 and 508 such that control module 60 may only measure and analyze the amplitudes of FF cardiac events that have similar morphologies.

Figure 6:
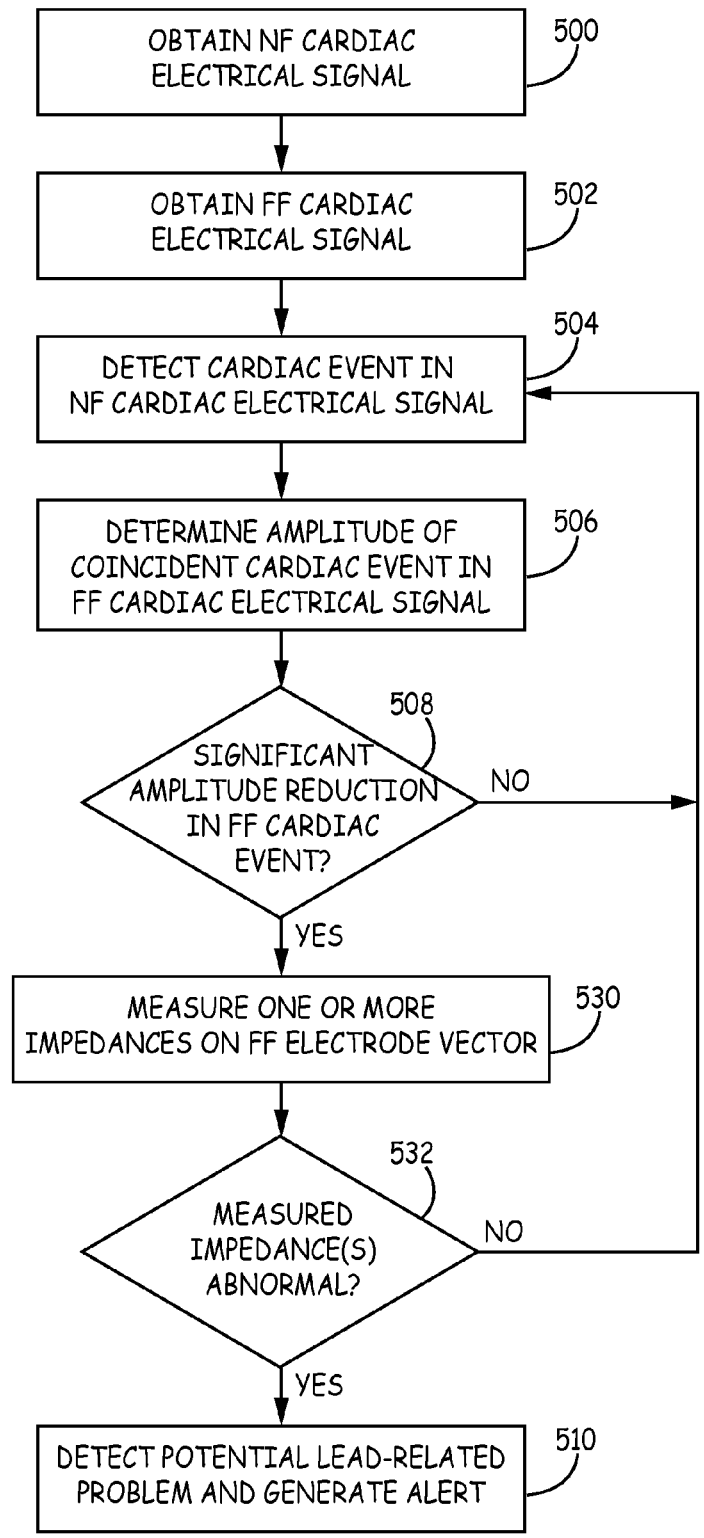
FIG. 6 is a flow diagram illustrating example operation of an IMD monitoring cardiac electrical signals to identify lead-related problems.

FIG. 6 is a flow diagram illustrating example operation of an IMD, such as IMD 10, monitoring cardiac electrical signals and lead impedance to identify lead-related problems. However, the techniques described with respect to FIG. 6 may be performed by an external device doing post processing of sensed cardiac electrical signals. The steps or operations performed in blocks 500, 502, 504, 506, 508, and 510 are the same as described above with respect to FIG. 4. As such, the repetitive description of those steps will not be repeated here, but are incorporated from above.

Control module 60 obtains a NF cardiac electrical signal sensed using a NF sensing vector between a pair of electrodes located in the same heart chamber for which events are being sensed (500). Control module 60 also obtains a FF cardiac electrical signal sensed using a FF sensing vector between at least one electrode located outside the heart chamber for which events are being sensed, in either a different heart chamber or even outside the heart (502). Control module 60 (or sensing module 106) detects a NF cardiac event (e.g., an R-wave event) in the NF cardiac electrical signal (504). Control module 60 determines the amplitude of a FF cardiac events in the FF cardiac electrical signal coincident with the detected cardiac events in the NF cardiac electrical signal (506).

Control module 60 determines whether there is a significant amplitude reduction in the coincident FF cardiac event (508). When control module 60 determines that there is not a significant amplitude reduction in the coincident FF cardiac event ("NO" branch of block 508), control module 60 (possibly in conjunction with sensing module 106) detects a next NF cardiac event (504). When control module 60 determines that there is a significant amplitude reduction in the coincident FF cardiac event ("YES" branch of block 508), control module 60 may measure one or more impedances on the FF sensing vector used to sense the FF cardiac electrical signal (530). Techniques for measuring the one or more impedance values of the FF sensing vector are described above with respect to FIG. 2.

Control module 60 determines whether one or more of the measured impedances are abnormal (532). Control module 60 may, for example, compare the one or more measured impedances to an impedance threshold and determine that an impedance measurement is abnormal when it is less than the impedance threshold. The impedance threshold may be dynamic (changes based on recently measured baseline impedance values, e.g., 25% decrease from baseline) or fixed (e.g. <20 ohms). When control module 60 determines that one or more of the measured impedances is abnormal, e.g., less than a threshold impedance ("YES" branch of block 532), control module 60 detects a lea problem (e.g., short-circuit of a conductor of the FF sensing vector) and generates an alert (510). When control module 60 determines that none of the measured impedances are abnormal, e.g., none of the impedance measurements are less than the threshold impedance ("NO" branch of block 532), control module 60 (possibly in conjunction with sensing module 106) detects a next NF cardiac event, determines the amplitude of the coincident FF cardiac event, and determines whether there is a significant amplitude reduction in the coincident FF cardiac event (504, 506, and 508).

Figure 7:
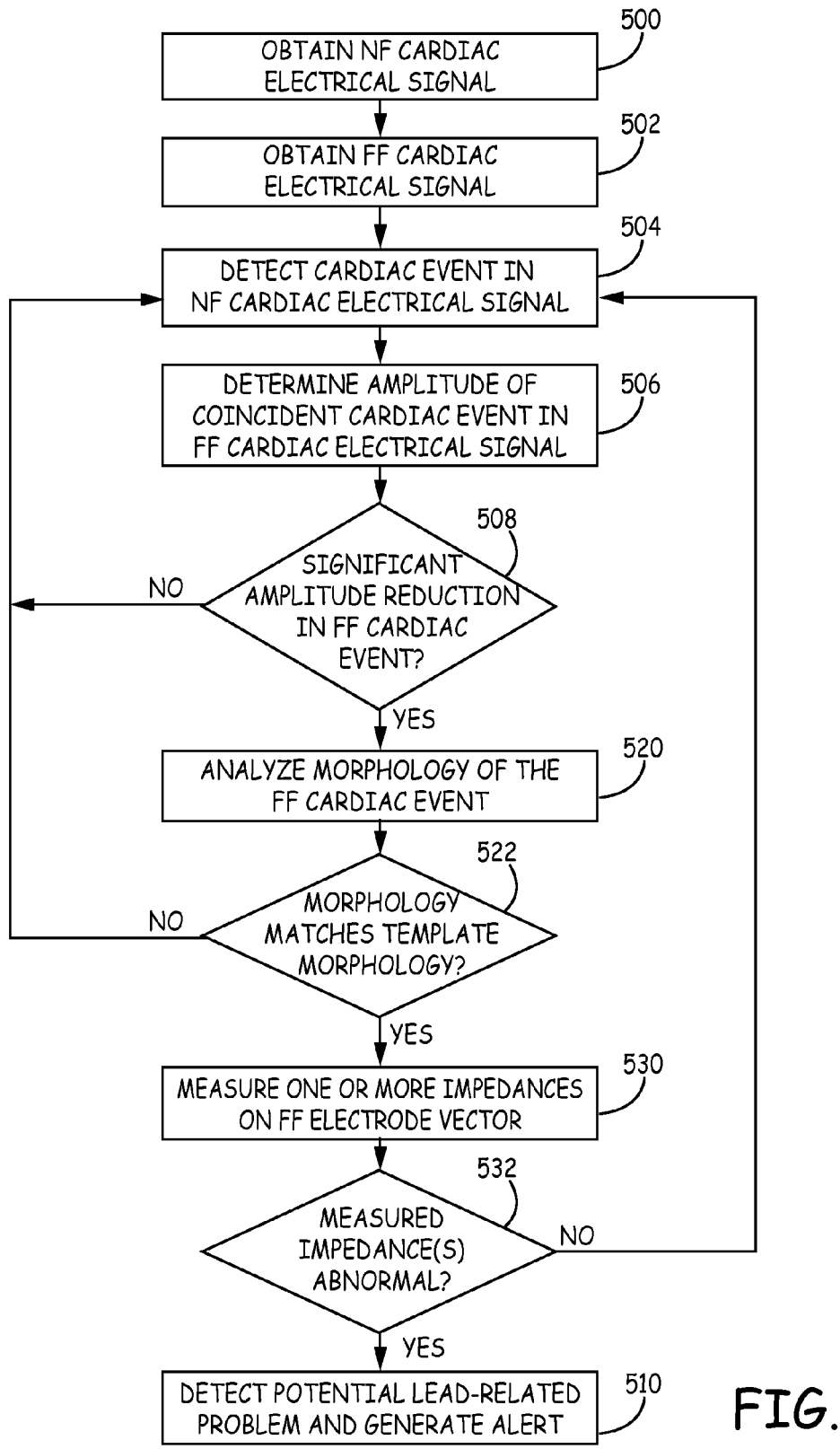
FIG. 7 is a flow diagram illustrating example operation of an IMD monitoring cardiac electrical signals to identify lead-related problems.

FIG. 7 is a flow diagram illustrating example operation of an IMD, such as IMD 10, monitoring cardiac electrical signals and lead impedance to identify lead-related problems. However, the techniques described with respect to FIG. 7 may be performed by an external device doing post processing of sensed cardiac electrical signals. The steps or operations performed in blocks 500, 502, 504, 506, 508, 510, 520, 522, 530, and 532 are the same as described above with respect to FIGS. 4, 5, and 6. As such, the detailed description of those blocks will not be repeated here, but are incorporated from above.

Control module 60 obtains a NF cardiac electrical signal sensed using a NF sensing vector between a pair of electrodes located in the same heart chamber for which events are being sensed (500). Control module 60 also obtains a FF cardiac electrical signal sensed using a FF sensing vector between at least one electrode located outside the heart chamber for which events are being sensed, in either a different heart chamber or even outside the heart (502). Control module 60 (or sensing module 106) detects a cardiac event (e.g., an R-wave event) in the NF cardiac electrical signal (504). Control module 60 determines the amplitudes of a FF cardiac event in the FF cardiac electrical signal coincident with the detected cardiac events in the NF cardiac electrical signal (506).

Control module 60 determines whether there is a significant amplitude reduction in the coincident FF cardiac event (508). When control module 60 determines that there is not a significant amplitude reduction in the coincident FF cardiac event ("NO" branch of block 508), control module 60 (possibly in conjunction with sensing module 106) detects a next NF cardiac event (504). When control module 60 determines that there is a significant amplitude reduction in the coincident FF cardiac event ("YES" branch of block 508), control module 60 analyzes a morphology of the FF cardiac electrical signal that includes the coincident FF cardiac event (520). When control module 60 determines that the morphology of the FF cardiac electrical signal that includes the coincident FF cardiac event does not match the morphology template ("NO" branch of block 522), control module 60 (possibly in conjunction with sensing module 106) detects a next NF cardiac event, determines the amplitude of the FF cardiac event coincident with the detected NF cardiac event, and determines whether there is a significant amplitude reduction in the coincident FF cardiac event (504, 506, and 508).

When control module 60 determines that the morphology of the FF cardiac electrical signal that includes the coincident FF cardiac event matches the morphology template ("YES" branch of block 522), control module 60 measures one or more impedances on the FF sensing vector used to sense the FF cardiac electrical signal (530). Control module 60 determines whether one or more of the measured impedances are abnormal (532). When control module 60 determines that one or more of the measured impedances is abnormal, e.g., is less than a threshold impedance ("YES" branch of block 532), control module 60 detects a lead problem (e.g., short-circuit of a conductor of the FF sensing vector) and generates an alert (510). When control module 60 determines that none of the measured impedances are abnormal ("NO" branch of block 532), control module 60 (possibly in conjunction with sensing module 106) detects a next NF cardiac event, determines the amplitude of the coincident FF cardiac event, and determines whether there is a significant amplitude reduction in the coincident FF cardiac event (504, 506, and 508).

Figure 8:
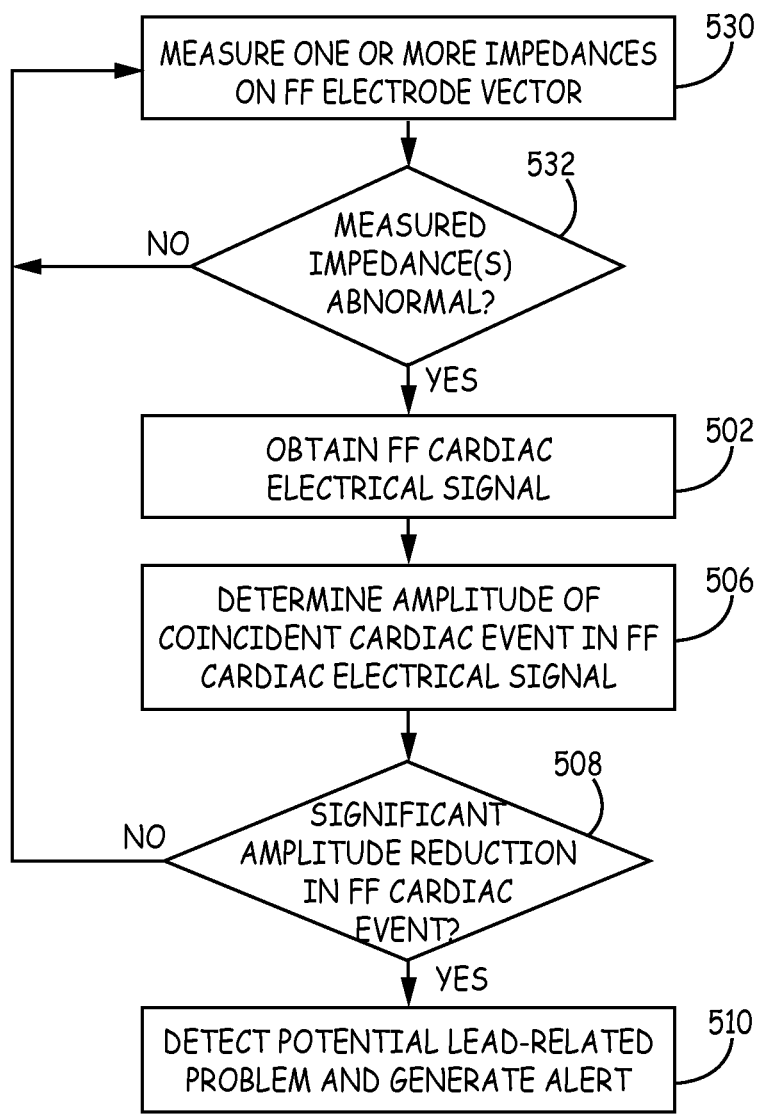
FIG. 8 is a flow diagram illustrating example operation of an IMD monitoring cardiac electrical signals and lead impedance to identify lead-related problems.

FIG. 8 is a flow diagram illustrating example operation of an IMD, such as IMD 10, monitoring cardiac electrical signals and lead impedance to identify lead-related problems. However, the techniques described with respect to FIG. 8 may be performed by an external device doing post processing of sensed cardiac electrical signals. The steps or operations performed in blocks 500, 502, 504, 506, 508, 510, 520, and 522 are the same as described above with respect to FIGS. 4, 5, and 6. As such, the detailed description of those blocks will not be repeated here, but are incorporated from above.

Control module 60 measures one or more impedances on the FF sensing vector used to sense the FF cardiac electrical signal (530). Control module 60 may, in one example, measure the impedances on the FF sensing vector in response to detecting a NF cardiac event. Control module may measure the one or more impedances on a periodic basis, in response to a trigger, or at other times. Control module 60 determines whether one or more of the measured impedances are abnormal (532). When control module 60 determines that the measured impedances are not abnormal ("NO" branch of block 532), control module 60 continues to measure one or more subsequent impedances of the FF sensing vector (530). The subsequent impedance measurements may be during the current impedance measurement period or a subsequently triggered impedance measurement period.

When control module 60 determines that one or more of the measured impedances abnormal, e.g., are less than an impedance threshold ("YES" branch of block 532), control module 60 obtains a FF cardiac electrical signal sensed using a FF sensing vector (502). The FF cardiac electrical signal may be sensed after the abnormal impedance measurement(s). Alternatively, control module 60 may obtain the FF cardiac electrical signal from memory 56. In this case, the FF cardiac electrical signal may include portions before and after the time at which the abnormal impedance measurement(s) was (were) obtained.

Control module 60 determines the amplitude of the FF cardiac event in the FF cardiac electrical signal coincident with detected cardiac events in the NF cardiac electrical signal (506). In one example, control module 60 may determine the amplitude of the FF cardiac electrical signal within a window of time that is based on when the impedance measurement is taken. In another example, control module 60 may determine the amplitude of the FF cardiac electrical signal within a window of time that is based on when NF cardiac event is sensed on the NF cardiac electrical signal.

When control module 60 determines that there is a significant amplitude reduction in the coincident FF cardiac event ("YES" branch of block 508), control module 60 detects a lead problem (e.g., short-circuit of conductor of the FF sensing vector) and generate an alert (510). When control module 60 determines that there is not a significant amplitude reduction in the coincident FF cardiac event ("NO" branch of block 508), control module 60 measures a subsequent impedance on the FF electrode vector (530).

Although not illustrated in FIG. 8, control module 60 may analyze a morphology of the FF cardiac electrical signal that includes the coincident FF cardiac event in addition to analyzing for a significant amplitude reduction in the coincident FF cardiac electrical signal. As such, control module may, in some embodiments, detect the potential lead-related problem and generate the alert in block 510 only when there is a significant amplitude reduction in the coincident FF cardiac event and the morphology of the FF cardiac electrical signal that includes the coincident FF cardiac event having the significant amplitude reduction matches a morphology template. In other words, the steps of blocks 520 and 522 may performed between block 508 and 510 in FIG. 8.

Various combinations or modifications of the illustrative embodiments may be conceived by one having ordinary skill in the art based on the teachings provided herein. For example, the techniques disclosed herein may be performed in a different order or combination than shown and described in conjunction with the drawings. It is appreciated that various modifications to the referenced embodiments may be made without departing from the scope of the disclosure and the following claims.

The invention claimed is:

1. A method comprising:
obtaining a near-field (NF) cardiac electrical signal sensed via a NF sensing vector between a first pair of electrodes located within a first chamber of a heart;
obtaining a far-field (FF) cardiac electrical signal sensed via a FF sensing vector between a second pair of electrodes, wherein at least one of the second pair of electrodes is located outside the first heart chamber of the heart;
detecting a NF cardiac event in the NF cardiac electrical signal;
determining an amplitude of a FF cardiac event in the FF cardiac electrical signal coincident the detected NF cardiac event;
comparing the amplitude of the coincident FF cardiac event to a threshold amplitude; and
detecting a short circuit condition on the FF sensing vector when the amplitude of the coincident FF cardiac event is less than the threshold amplitude.

2. The method of claim 1, further comprising:
in response to the amplitude of the coincident FF cardiac event being less than the threshold amplitude, comparing a morphology of a portion of the FF cardiac electrical signal that includes the coincident FF cardiac event to a morphology template,
wherein detecting the presence of the short circuit condition comprises detecting the presence of the short circuit condition when the amplitude of the coincident FF cardiac event is less than the threshold amplitude and the morphology of the coincident FF cardiac event matches the morphology template.

3. The method of claim 2, wherein the comparing of the morphology of the portion of the FF cardiac electrical signal that includes the coincident FF cardiac event to the morphology template is independent of amplitude.

4. The method of claim 2, further comprising:
in response to the amplitude of the coincident FF cardiac event being less than the threshold amplitude and the morphology of the coincident FF cardiac event matching the morphology template, obtaining one or more impedance measurements of the FF sensing vector; and
comparing the one or more impedance measurements of the FF sensing vector to an impedance threshold;
wherein detecting the presence of the short circuit condition comprises detecting the presence of the short circuit condition when the amplitude of the coincident FF cardiac event is less than the threshold amplitude, the morphology of the coincident FF cardiac event matches the morphology template, and at least one of the one or more impedance measurements is less than the impedance threshold.

5. The method of claim 1, wherein obtaining the FF cardiac electrical signal sensed via the FF sensing vector comprises obtaining a FF cardiac electrical signal sensed via a FF sensing vector between a first electrode on a lead and a second electrode on a housing of the an implantable medical device.

6. The method of claim 1, further comprising:
in response to the amplitude of the coincident FF cardiac event being less than the threshold amplitude, obtaining one or more impedance measurements of the FF sensing vector; and
comparing the one or more impedance measurements of the FF sensing vector to an impedance threshold;
wherein detecting the presence of the short circuit condition comprises detecting the presence of the short circuit condition when the amplitude of the coincident FF cardiac event is less than the threshold amplitude and at least one of the one or more impedance measurements is less than the impedance threshold.

7. The method of claim 1, further comprising periodically sensing the FF cardiac electrical signal via the FF sensing vector.

8. The method of claim 1, further comprising sensing the FF cardiac electrical signal via the FF sensing vector in response to detecting at least one of a pre-identified heart rate, a pre-identified motion, a pre-identified pressure, a pre-identified respiration, and a pre-identified body posture.

9. The method of claim 1, further comprising:
periodically obtaining one or more impedance measurements of the FF sensing vector; and
comparing the one or more impedance measurements of the FF sensing vector to an impedance threshold;
in response to at least one of the one or more impedance measurements being less than the impedance threshold, sensing a far-field (FF) cardiac electrical signal via the FF sensing vector.

10. The method of claim 1, wherein the threshold amplitude is determined based on the amplitude of one or more previously detected cardiac events.

11. An implantable medical system comprising:
at least one medical electrical lead including:
a plurality of electrodes carried by the at least one medical electrical lead; and
a plurality of electrical conductors, each of the plurality of electrical conductors electrically connected to a respective one of the plurality of electrodes;
an implantable medical device electrically coupled to the at least one medical electrical lead, the implantable medical device including:
a housing at least partially formed of a conductive material, the conductive material forming a housing electrode;
a sensing module electrically coupled to a near field (NF) sensing vector between a first pair of electrodes of the plurality of electrodes carried by the lead and located within a first chamber of a heart to obtain a NF cardiac electrical signal and electrically coupled to a far-field (FF) sensing vector between a second pair of electrodes, at least one of the second pair of electrodes being located outside the first heart chamber of the heart, to obtain a FF cardiac electrical signal;
a control module electrically coupled to the sensing module, wherein the control module detects a NF cardiac event in the NF cardiac electrical signal, determines an amplitude of a FF cardiac event in the FF cardiac electrical signal coincident the detected NF cardiac event, compares the amplitude of the coincident FF cardiac event to a threshold amplitude, and detects a short circuit condition on the FF sensing vector when the amplitude of the coincident FF cardiac event is less than the threshold amplitude.

12. The implantable medical system of claim 11, wherein the control module, in response to the amplitude of the coincident FF cardiac event being less than the threshold amplitude, compares a morphology of a portion of the FF cardiac electrical signal that includes the coincident FF cardiac event to a morphology template and detects the presence of the short circuit condition when the amplitude of the coincident FF cardiac event is less than the threshold amplitude and the morphology of the coincident FF cardiac event matches the morphology template.

13. The implantable medical system of claim 12, wherein the control module compares the morphology of the portion of the FF cardiac electrical signal that includes the coincident FF cardiac event to the morphology template in a manner that is independent of amplitude.

14. The implantable medical system of claim 12, further comprising:
an impedance measurement module that, in response to the amplitude of the coincident FF cardiac event being less than the threshold amplitude and the morphology of the coincident FF cardiac event matching the morphology template, obtains one or more impedance measurements of the FF sensing vector,
wherein the control module compares the one or more impedance measurements of the FF sensing vector to an impedance threshold and detects the presence of the short circuit condition when the amplitude of the coincident FF cardiac event is less than the threshold amplitude, the morphology of the coincident FF cardiac event matches the morphology template, and at least one of the one or more impedance measurements is less than the impedance threshold.

15. The implantable medical system of claim 11, wherein the second pair of electrodes of the FF sensing vector comprises a first electrode of the plurality of electrodes carried on the lead and the housing electrode.

16. The implantable medical system of claim 11, wherein the second pair of electrodes of the FF sensing vector comprises a first electrode of the plurality of electrodes carried on the lead and a second electrode of the plurality of electrodes carried on the lead, the second electrode of the plurality of electrodes carried on the lead being located outside the first heart chamber of the heart.

17. The implantable medical system of claim 11, further comprising:
an impedance measurement module that, in response to the amplitude of the coincident FF cardiac event being less than the threshold amplitude, obtains one or more impedance measurements of the FF sensing vector, wherein the control module compares the one or more impedance measurements of the FF sensing vector to an impedance threshold and detects the presence of the short circuit condition when the amplitude of the coincident FF cardiac event is less than the threshold amplitude and at least one of the one or more impedance measurements is less than the impedance threshold.

18. The implantable medical system of claim 11, further comprising:

a physiological sensor configured to measure at least one of motion, pressure, respiration, or body posture, wherein the control module detects at least one of a pre-identified motion, a pre-identified pressure, a pre-identified respiration, or a pre-identified body posture based on the output of the physiological sensor and controls the sensing module to obtain the FF cardiac electrical signal via the FF sensing vector in response to detecting at least one of a pre-identified motion, a pre-identified pressure, a pre-identified respiration, and a pre-identified body posture.

19. The implantable medical system of claim 11, further comprising:

an impedance measurement module that periodically obtains one or more impedance measurements of the FF sensing vector, wherein the control module compares the one or more impedance measurements of the FF sensing vector to an impedance threshold and in response to at least one of the one or more impedance measurements being less than the impedance threshold, controls the sensing module to obtain the FF cardiac electrical signal via the FF sensing vector.

20. The implantable medical system of claim 11, wherein the threshold amplitude is determined based on the amplitude of one or more previously detected cardiac events.

21. The implantable medical system of claim 11, wherein the sensing module includes:

a first sensing channel that obtains the NF cardiac electrical signal via the NF sensing vector, the first sensing channel including a first sensing amplifier; and a second sensing channel the obtains the FF cardiac electrical signal via the FF sensing vector, the second sensing channel including a second sensing amplifier that is periodically powered on to obtain the FF cardiac electrical signal via the FF sensing vector.

* * * * *